(12) United States Patent
Okajima et al.

(10) Patent No.: US 11,074,997 B2
(45) Date of Patent: Jul. 27, 2021

(54) MULTI-MODAL ENCRYPTED MESSAGING SYSTEM

(71) Applicant: Statum Systems Inc., Wellesley, MA (US)

(72) Inventors: Stephen Michael Okajima, Boston, MA (US); Arman Serebrakian, Boston, MA (US); Ara Nazarian, Wellesley, MA (US)

(73) Assignee: Statum Systems Inc., Wellesley, MA (US)

( * ) Notice: Subject to any disclaimer, the term of this patent is extended or adjusted under 35 U.S.C. 154(b) by 115 days.

(21) Appl. No.: 16/377,564

(22) Filed: Apr. 8, 2019

(65) Prior Publication Data

US 2019/0237170 A1    Aug. 1, 2019

Related U.S. Application Data

(63) Continuation-in-part of application No. 15/877,986, filed on Jan. 23, 2018.

(51) Int. Cl.
| | |
|---|---|
| *G16H 10/60* | (2018.01) |
| *H04L 9/08* | (2006.01) |
| *H04L 29/06* | (2006.01) |
| *G06F 21/62* | (2013.01) |
| *H04L 29/08* | (2006.01) |

(52) U.S. Cl.
CPC ......... *G16H 10/60* (2018.01); *G06F 21/6209* (2013.01); *G06F 21/6245* (2013.01); *H04L 9/088* (2013.01); *H04L 9/0844* (2013.01); *H04L 9/0891* (2013.01); *H04L 9/0894* (2013.01); *H04L 63/061* (2013.01); *H04L 67/02* (2013.01)

(58) Field of Classification Search
CPC . H04W 12/00; H04W 12/001; H04W 12/002; H04W 12/003; H04W 12/004; H04W 12/005; H04W 12/00502; H04W 12/0051; H04W 12/06; H04W 12/0602; H04W 12/0605; H04W 12/0608; H04W 12/609; H04W 12/08; H04W 12/10; G06F 21/64; G06F 2221/2107; G06F 21/62
See application file for complete search history.

(56) References Cited

U.S. PATENT DOCUMENTS

| | | | |
|---|---|---|---|
| 5,978,837 A | 11/1999 | Foladare et al. | |
| 7,093,137 B1 * | 8/2006 | Sato ................... | G06F 21/6227 380/277 |
| 2005/0170869 A1 | 8/2005 | Slemmer et al. | |
| 2010/0305966 A1 | 12/2010 | Coulter et al. | |
| 2012/0004961 A1 | 1/2012 | Flynn | |

(Continued)

OTHER PUBLICATIONS

"U.S. Appl. No. 15/877,986, filed May 7, 2020 to Final Office Action dated Feb. 27, 2020", 12 pages.

(Continued)

*Primary Examiner* — Jean A Gelin
(74) *Attorney, Agent, or Firm* — Schwegman Lundberg & Woessner, P.A.

(57) ABSTRACT

A multi-modal encrypted messaging platform to provide HIPAA compliant messaging and interfaces to provide access to electronic data records. The proposed invention discloses example embodiments that comprise a server-system, a client device in communication with the server-system, and an auxiliary device coupled to the client device.

17 Claims, 7 Drawing Sheets

(56) References Cited

U.S. PATENT DOCUMENTS

| | | |
|---|---|---|
| 2013/0259028 A1 | 10/2013 | Skala |
| 2013/0318347 A1* | 11/2013 | Moffat ................. H04L 9/0894 713/168 |
| 2014/0229737 A1* | 8/2014 | Roth .................... H04L 9/0618 713/176 |
| 2014/0229739 A1* | 8/2014 | Roth .................. H04L 63/0442 713/189 |
| 2014/0325217 A1* | 10/2014 | Mori ....................... H04L 9/008 713/165 |
| 2015/0172881 A1 | 6/2015 | Huang et al. |
| 2015/0181171 A1 | 6/2015 | Park |
| 2015/0248357 A1* | 9/2015 | Kaplan ............... G06F 12/1036 713/193 |
| 2016/0007271 A1 | 1/2016 | Plicanic Samuelsson et al. |
| 2016/0057156 A1* | 2/2016 | Lin ......................... H04W 4/14 713/170 |
| 2017/0344646 A1* | 11/2017 | Antonopoulos .... G06F 16/2453 |
| 2018/0048464 A1* | 2/2018 | Lim ..................... H04L 9/0894 |
| 2018/0205715 A1 | 7/2018 | Ingale et al. |
| 2019/0182216 A1* | 6/2019 | Gulak .................... G16H 10/60 |
| 2019/0230622 A1 | 7/2019 | Okajima et al. |

OTHER PUBLICATIONS

"U.S. Appl. No. 15/877,986, Non Final Office Action dated Jun. 8, 2020", 6 pages.

"U.S. Appl. No. 15/877,986, Examiner Interview Summary dated Apr. 27, 2020", 3 pages.

"U.S. Appl. No. 15/877,986, Final Office Action dated Feb. 27, 2020", 54 pgs.

"U.S. Appl. No. 15/877,986, filed Sep. 3, 2020 to Non Final Office Action dated Jun. 8, 2020", 10 pages.

"U.S. Appl. No. 15/877,986, Examiner Interview Summary dated Nov. 25, 2019", 3 pgs.

"U.S. Appl. No. 15/877,986, filed Nov. 21, 2019 to Non-Final Office Action dated Aug. 22, 2019", 18 pgs.

"U.S. Appl. No. 15/877,986, Non Final Office Action dated Aug. 22, 2019", 51 pgs.

* cited by examiner

MULTI-MODAL ENCRYPTED MESSAGING SYSTEM

CLAIM OF PRIORITY

This application is a continuation-in-part application of and claims priority benefit from U.S. patent application Ser. No. 15/877,986, filed on Jan. 23, 2018 and entitled "ENHANCED PAGER NETWORK," and which is hereby incorporated by reference herein in its entirety.

TECHNICAL FIELD

The present invention relates to encrypted messaging systems.

BACKGROUND

The Health Insurance Portability and Accountability Act (HIPAA), as well as a number of other compliance standards, exist to define and provide communication and privacy rules and definitions for various fields and industries. Such compliance standards seek to allow for the modernization of the flow of information, while addressing the potential of fraud, theft, and privacy.

For example, HIPAA set out strict requirements for the control and transmission of electronic medical data over networks, wherein the transfer of such data must be encrypted if transferred over an open network, or alternatively, much be accessed and transferred on a closed and secured system or network, if the data is to remain unencrypted. HIPAA therefore benefits patients and doctors alike, by providing requirements to ensure the privacy and security of medical information.

A system to provide a platform to facilitate access to electronic medical data, while maintaining full compliance to HIPAA requirement would therefore prove to be a beneficial improvement in existing messaging technologies.

BRIEF DESCRIPTION OF THE DRAWINGS

Some embodiments are illustrated by way of example and not limitation in the figures of the accompanying drawings in which.

DETAILED DESCRIPTION

Figure 1:
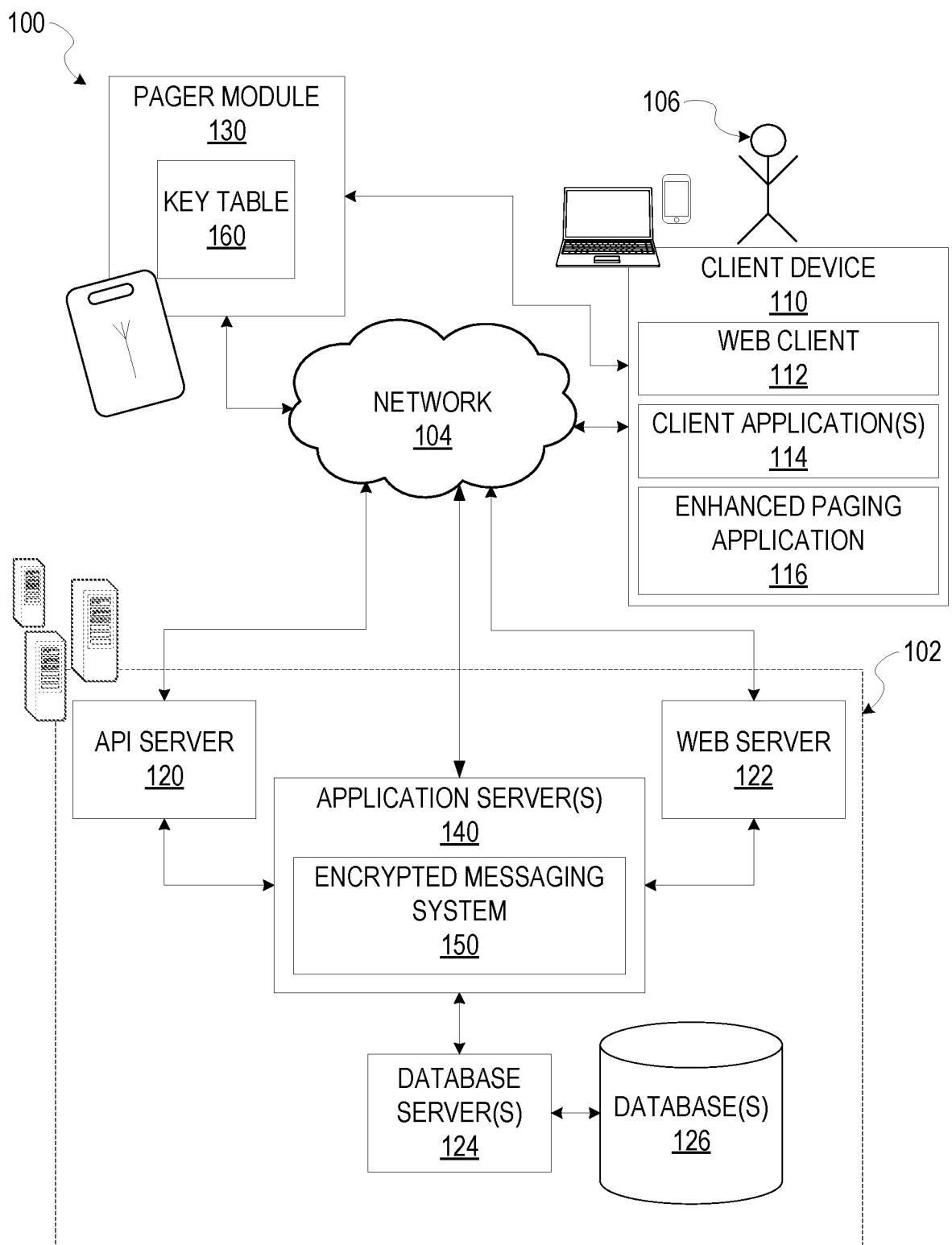
FIG. 1 is a network diagram depicting a client-server system, within which one example embodiment may be deployed.

Reference will now be made in detail to specific example embodiments for carrying out the inventive subject matter. Embodiments may be practiced without some or all of these details. It will be understood that the forgoing disclosure is not intended to limit the scope of the claims to the described embodiments. On the contrary, it is intended to cover alternatives, modifications, and equivalents as may be included within the scope of the disclosure as defined by the appended claims. In addition, well known features may not have been described in detail to avoid unnecessarily obscuring the subject matter.

Disclosed embodiments discuss systems and methods for a multi-modal encrypted messaging platform to provide HIPAA compliant messaging and interfaces to provide access to electronic data records. The proposed invention discloses example embodiments that comprise a server-system, a client device in communication with the server-system, and an auxiliary device coupled to the client device. As used herein, "coupled to" generally refers to a connection between components, which can be an indirect communicative connection or direct communicative connection (e.g., without intervening components), whether wired or wireless, including connections such as electrical, optical, magnetic, etc.

According to certain embodiments, the system is configured to perform operations that include: receiving a request at a server system, wherein the request includes a set of request attributes that include a user or device identifier; generating an encryption key in response to the receiving the request, wherein the encryption key may be generated based on at least a portion of the request attributes; assigning the encryption key to a request instance associated with the request at a user account identified by the user or device identifier; encrypting a data record based on the encryption key responsive to the request; and communicating a presentation of the encrypted data record to the client device associated with the user account, whereby the client device may decrypt the encrypted data record based on the encryption key.

The system may employ a Diffie-Hellman key exchange protocol, wherein a public portion of the encryption key is generated in response to requests received at the server-system from one or more client devices. Responsive to generating an encryption key based on request attributes of a request, the system may be configured to transmit the public portion of the encryption key to an auxiliary device coupled with the client device. In some embodiments, transmitting the public portion of the encryption key may include transmitting the public portion of the encryption key through a specific communication channel specified by a preselected frequency (e.g., in the VHF or UHF bands). The client device may thereby retrieve the public portion of the encryption key from the auxiliary device to decrypt the data record.

From a user perspective, a user of a client device may generate and provide a request to a server system, wherein the request comprises an identification of a data record stored within the server system. Responsive to receiving the request to access the data record at the server system, the system parses the request to extract a set of request attributes that may include a user identifier associated with the client device. The system applies one or more encryption protocols, including but not limited to a Diffie-Hellman key exchange protocol, to generate an encryption key, and delivers the encryption key to an auxiliary device coupled to the client device, where the encryption key is indexed and stored at a memory location corresponding with the request instance. The system may then encrypt the data object, and either save a copy of the encrypted data object at a memory location at the server system, or deliver the encrypted data object to the client device itself In some example embodiments, administrators may assign access restrictions and criteria to data records, such that the access restrictions and criteria define rules and credentials to access the data record. For example, in such embodiments, the data records may include reference identifiers, and the system may perform operations that include: retrieving access restrictions associated with the data record from a repository based on the reference identifier that identifies the data record, wherein the access restriction includes at least a condition; applying the access restriction to the encryption key at the request instance associated with a request to access the data record at the user account identified by the user identifier; detecting an occurrence of the condition; and denying subsequent requests to access the data record from the client device.

For example, the access condition may include one or more of: temporal constraints that define periods of time that the data record may be accessed or viewed; user attributes required to receive access to the data record; certain security credentials; as well as geo-location conditions. The system may thereby manage access to each data record based on the associated access conditions of the data record.

In some embodiments, to remove access to a data record for a client device, the system deletes the encryption key from the request instance within the user account identified by the user identifier, in response to detecting (or detecting an absence of) the one or more access conditions associated with a given data record.

As an illustrative example from a user perspective, a user may provide an input that comprises a request for a data record via an interface presented at a client device. The request to access the data record may include contextual data that includes one or more of a user identifier associated with the user, an identification of the requested data record, device information (i.e., MAC addresses, specific hardware codes, RFID code), biometric data, time and date information, geolocation information, barometric pressure, acceleration and device orientation, as well as compass positioning.

Responsive to receiving the request to access the data record, the system generates an encryption key based on at least a portion of the contextual data from the request to access the data record. By utilizing a diverse pool of contextual data, a much stronger encryption key may be generated. For example, in certain embodiments, the system may apply a predefined hash function to a portion of the contextual data in order to generate the encryption key.

As discussed above, the encryption key may be generated using a Diffie-Hellman key-exchange, whereby the system and the client device maintain corresponding sets of private variables and utilize a public variable to generate and exchange encryption keys. The system may then assign the encryption key to a request instance associated with the request to access the data record, at a user account identified by the user identifier at a database of the system and transmit the encryption key to the auxiliary device coupled with the client device.

The system may then encrypt the data record using the encryption key assigned to the request instance from the user account identified by the user identifier and communicate the encrypted data record to the client device. The client device may then receive the encrypted data record and access the auxiliary device to retrieve the corresponding encryption key. Responsive to retrieving the encryption key from the auxiliary device, the client device may cause display of a presentation of the data record. The data record is therefore encrypted before and during transmission, maintaining full HIPAA compliance.

As discussed above, in certain instances, the data records may include an associated set of access conditions or restrictions. For example, a data record may be assigned certain access conditions that limit or restrict access to the data record to users/devices located within a defined geofence, as well as certain temporal constraints that limit access to the data record to a period of time, time of day, or duration of event. Responsive to detecting (or detecting an absence of) one or more of the above conditions, the system deletes the encryption key at the request instance associated with the request to access the data record within the user account identified by the user identifier. Subsequent requests to access or view the data record may thereby be denied.

In some embodiments, communications to the auxiliary device from the server-system may be transmitted in a specified band of the radio spectrum, including the Very High Frequency (VHF), and in some instances Ultra High Frequency (UHF) bands. VHF, and in some instances, UHF, bands of the radio spectrum offer higher signal penetration and range that higher frequency bands typically used in Wi-Fi and cellular networks. Accordingly, communications between the server-system and the auxiliary device may be sent using 4-bit Binary-coded decimal (BCD) values, as well as 7-bit American Standard Code for Information Interchange (ASCII). Communications to the auxiliary device may therefore be encoded at the server-system based on the frequency relied upon, which may in some embodiments be variable based on attributes of the requests from the client device.

FIG. 1 is an example embodiment of a high-level client-server-based network architecture 100. A networked system 102, in the example form of a pager network, provides server-side functionality via a network 104 (e.g., the Internet or wide area network (WAN), Bluetooth) to one or more client devices 110. FIG. 1 illustrates, for example, a web client 112 (e.g., a browser, such as the Internet Explorer® browser developed by Microsoft® Corporation of Redmond, Wash. State), client application(s) 114, and an enhanced paging application 116 executing on the client device 110.

The client device 110 may comprise, but is not limited to, a wearable device, mobile phone, desktop computer, laptop, portable digital assistant (PDA), smart phone, tablet, ultrabook, netbook, laptop, multi-processor system, microprocessor-based or programmable consumer electronics, game console, set-top box, or any other communication device that a user may utilize to access the networked system 102. In some embodiments, the client device 110 comprises a display module (not shown) to display information (e.g., in the form of user interfaces). In further embodiments, the client device 110 comprises one or more of touch screens, accelerometers, gyroscopes, cameras, microphones, global positioning system (GPS) devices, and so forth. The client device 110 may be a device of a user configured to facilitate communication within the networked system 102. One or more portions of the network 104 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the public switched telephone network (PSTN), a cellular telephone network, a wireless network, a WiFi network, a WiMax network, a Wireless Mesh Network (WMN), or a combination of two or more such networks.

The client device 110 may include one or more client applications 114 (also referred to as "apps") such as, but not limited to, a web browser, messaging application, electronic mail (email) application, a navigation application, and the like. In some embodiments, the client application(s) 114 is configured to locally provide the user interface and at least some of the functionalities with the client application(s) 114 configured to communicate with the networked system 102, on an as needed basis, for data or processing capabilities not locally available (e.g., access to a database of items available for sale, to authenticate a user, to verify a method of payment). Conversely, the client device 110 may use its web browser to access data hosted on the networked system 102 to generate and provide various user interfaces.

One or more users 106 may be a person, a machine, or other means of interacting with the client device 110. In example embodiments, the user 106 is not part of the network architecture 100, but may interact with the network architecture 100 via the client device 110 or other means. For instance, the user 106 provides input (e.g., touch screen input, alphanumeric input, text-to-speech, or speech-to-text) to the client device 110 and the input is communicated to the networked system 102 via the network 104. In this instance, the networked system 102, in response to receiving the input from the user 106, communicates information to the client device 110 via the network 104 to be presented to the user 106. In this way, the user 106 can interact with the networked system 102 using the client device 110.

An application program interface (API) server 120 and a web server 122 are coupled to, and provide programmatic and web interfaces respectively to, one or more application servers 140. The application server(s) 140 may host an encrypted messaging system 150, for providing encrypted communications between an application server 140 (e.g., a server system), and the client device 110. For example, the encrypted messaging system 150 may generate encryption keys in response to requests from the client device 110 and transmit the encryption keys, or portions of the encryption keys, to an auxiliary device (e.g., the pager module 130) coupled to the client device 110. The client device 110 may then access the pager module 130 to retrieve the appropriate encryption keys received from the encrypted messaging system 150. For example, in some embodiments, the pager module 130 may include one or more memory components to host a key table 160, wherein the key table 160 is configured to maintain a list of encryption keys, which may be sorted or labeled based on a request instance, or an identifier of a data object (e.g., a message, media content, etc.). In such embodiments, the client device 110 may access the key table 160 of the pager module 130 to retrieve an encryption key that corresponds with an encrypted data object accessed by the client device 110.

While the client-server-based network architecture 100 shown in FIG. 1 employs a client-server architecture, the present inventive subject matter is of course not limited to such an architecture, and could equally well find application in a distributed, or peer-to-peer, architecture system, for example. The encrypted messaging system 150 could also be implemented as standalone software programs, which do not necessarily have networking capabilities.

The web client 112 may access the various publication and payment systems 142 and 144 via the web interface supported by the web server 122. Similarly, the enhanced paging application 116 accesses the various services and functions provided by the encrypted messaging system 150 via the programmatic interface provided by the API server 120. The enhanced paging application 116 may, for example, generate and cause display of notifications in response to receiving message data from an associated pager module 130.

Figure 2:
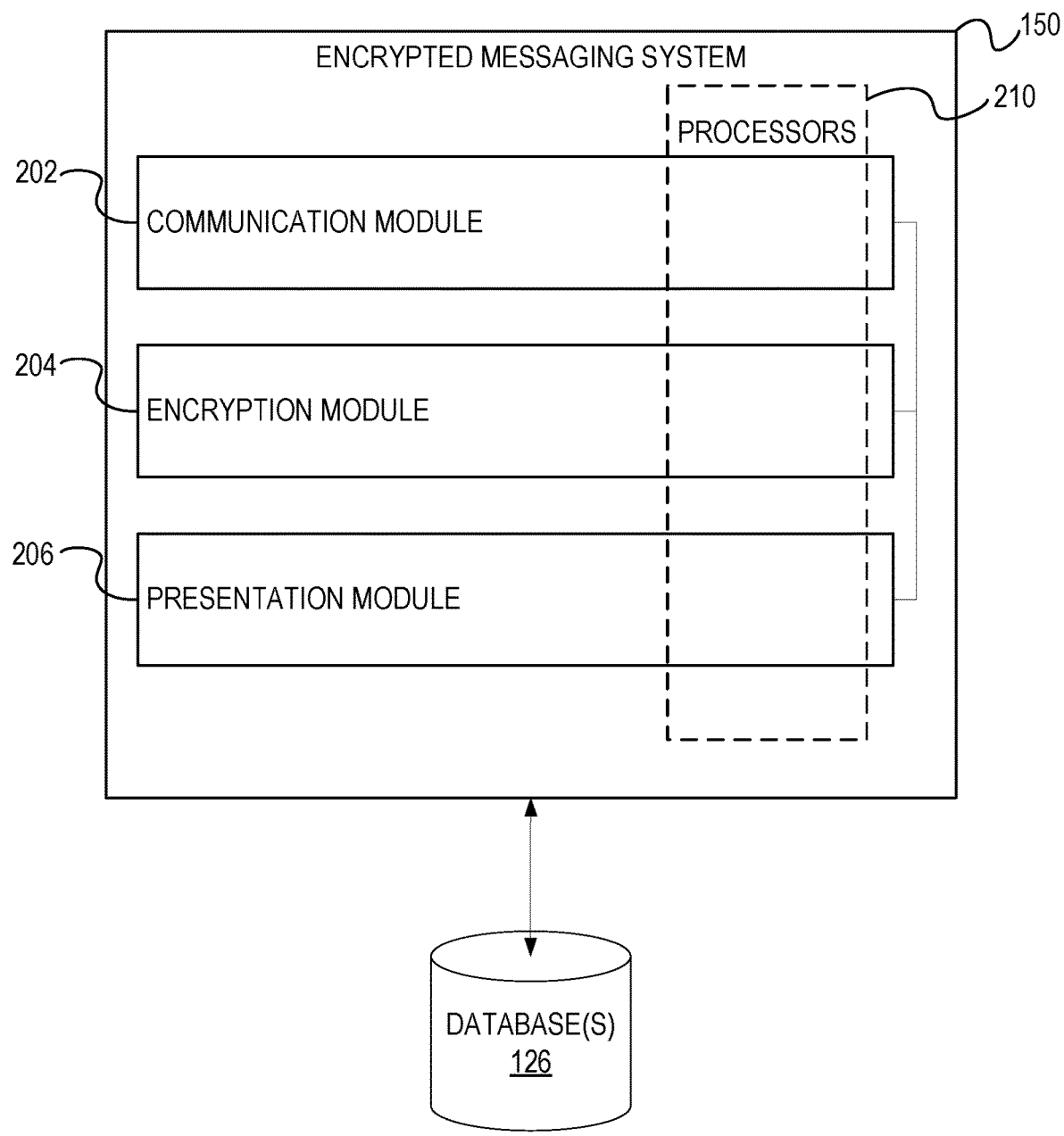
FIG. 2 is a block diagram illustrating components of an encrypted messaging system, according to some example embodiments.

FIG. 2 is a block diagram illustrating components of the encrypted messaging system 150 that configure the encrypted messaging system 150 to receive a request to access a data object from a client device 110, generate an encryption key in response to the request to access the data object, identify an auxiliary device (e.g., the pager module 130) associated (i.e., coupled with) the client device 110, transmit the encryption key or a portion of the encryption key to the pager module 130, encrypt the data object based on the encryption key (i.e., at the networked system 102), and communicate the encrypted data object to the client device 110, according to certain example embodiments. The encrypted messaging system 150 is shown as including a communication module 202, an encryption module 204, and a presentation module 206, all configured to communicate with each other (e.g., via a bus, shared memory, or a switch). Any one or more of these modules may be implemented using one or more processors 210 (e.g., by configuring such one or more processors 210 to perform functions described for that module) and hence may include one or more of the processors 210. In some embodiments, the modules of the encrypted messaging system 150 may be in coupled with the databases 126.

Any one or more of the modules described may be implemented using hardware alone (e.g., one or more of the processors 210 of a machine) or a combination of hardware and software. For example, any module described of the encrypted messaging system 150 may physically include an arrangement of one or more of the processors 210 (e.g., a subset of or among the one or more processors of the machine) configured to perform the operations described herein for that module. As another example, any module of the encrypted messaging system 150 may include software, hardware, or both, that configure an arrangement of one or more processors 210 (e.g., among the one or more processors of the machine) to perform the operations described herein for that module. Accordingly, different modules of the encrypted messaging system 150 may include and configure different arrangements of such processors 210 or a single arrangement of such processors 210 at different points in time. Moreover, any two or more modules of the encrypted messaging system 150 may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 3:
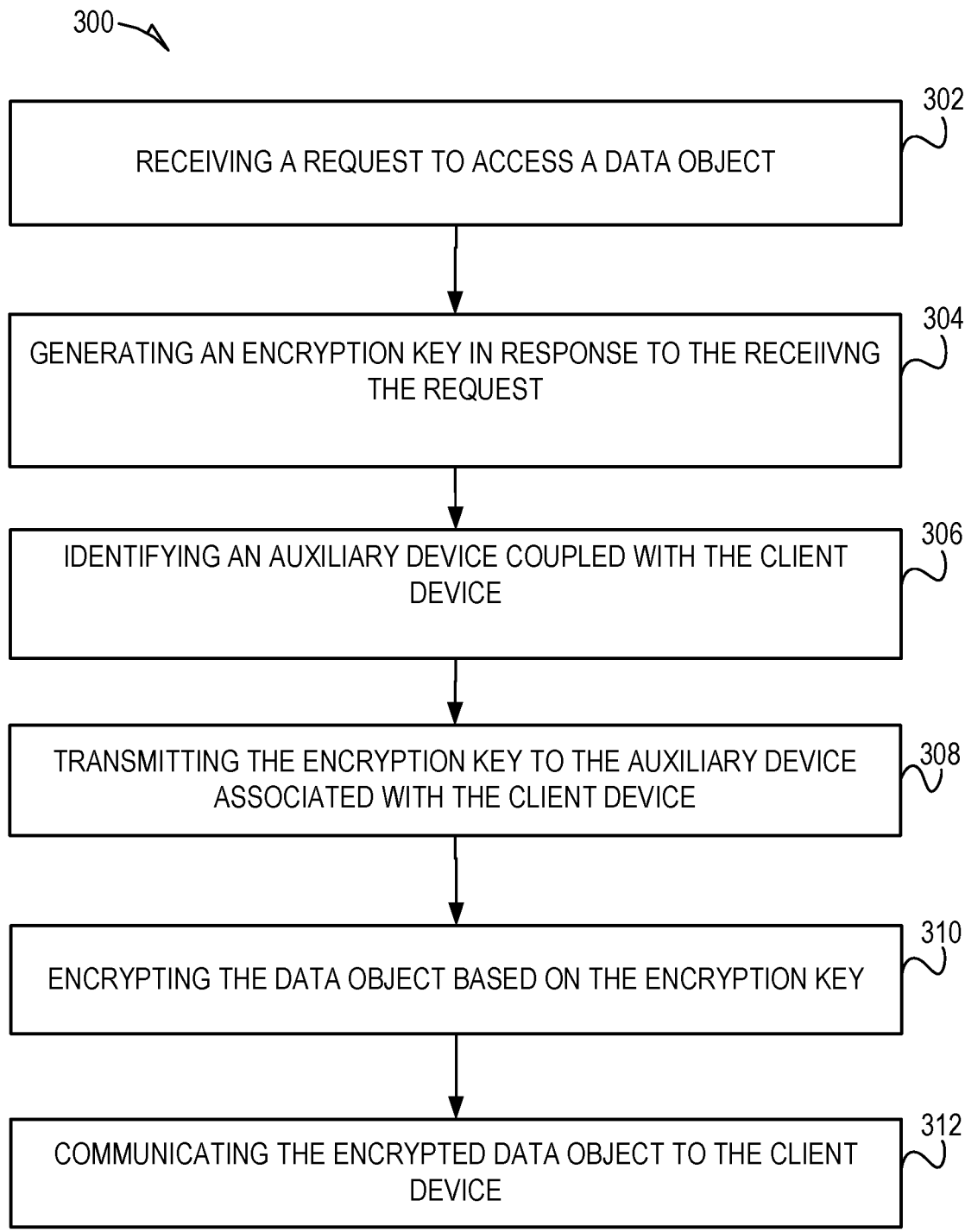
FIG. 3 is a flowchart illustrating operations of the encrypted messaging system in performing a method of encrypting a data object, according to some example embodiments.

FIG. 3 is a flowchart illustrating operations of the encrypted messaging system 150 in performing a method 300 of encrypting a data object, according to some example embodiments.

At operation 302, the communication module 202 receives a request to access a data object. The request may include an identification of a client device 110, and request data that includes one or more data objects that may include references to media content and message data. For example, the request may be received from the client device 110 itself, or from a third-party device or system in communication with the networked system 102.

At operation 304, the encryption module 204 generates one or more encryption keys in response to receiving the request, based on contextual data of the request. For example, as discussed above, the contextual data includes one or more of a user identifier, an identification of the requested data record, device information (i.e., MAC addresses, specific hardware codes, RFID code), biometric data, time and date information, geolocation information, barometric pressure, acceleration and device orientation, as well as compass positioning.

In some embodiments, the encryption module 204 may generate a single encryption key responsive to a request, while in further embodiments, the encryption module 204 generates a plurality of encryption keys. By doing so, a single communication exchange may provide a batch of future keys. For example, by providing a plurality of keys, data transfers for the purposes of key exchanges can be limited, thereby reducing the number of communications necessary, and data usage. The plurality of keys may be used in the case of communication loss.

In some embodiments, the encryption module 204 may generate the one or more encryption keys based on a Diffie-Hellman key exchange protocol, wherein one or more variables to generate the encryption key may be selected based on one or more attributes of the request or the client device 110.

In some embodiments, the encryption module 204 may define a request instance within the database 126 in response to receiving the request to access the data object, wherein the request instance comprises an identifier of the client device, an identification of the data object, and a record of the one or more encryption keys generated in response to the request, along with a sequence of the one or more encryption keys, such that as a first encryption key expires, a second encryption key may be selected based on the sequence.

At operation 306, the communication module 202 identifies an auxiliary device (i.e., the pager module 130) in response to the encryption module 204 generating the one or more encryption keys responsive to the request to access the data object. For example, the pager module 130 may be coupled with the client device 110 via one or more coupling methods that include NFC or Bluetooth, and wherein a record of the coupling of the client device 110 and the pager module 130 may be indexed and stored within a memory repository within the database 126.

In some embodiments, responsive to identifying the auxiliary device coupled with the client device 110, the encryption module 204 may update the request instance stored at the database 126 associated with the request from the client device 110, to include an identifier of the auxiliary device.

At operation 308, the communication module 202 transmits the one or more encryption keys, or a portion of the one or more encryption keys, to the auxiliary device coupled with the client device 110. In certain embodiments, the communication module 202 may transmit the one or more encryption keys or a portion of the one or more encryption keys to the auxiliary device via a specific range of radio frequency that the auxiliary device is specially configured to recognize and communicate through. In some embodiments the communication module 202 may communicate with the auxiliary device via one or more protocols that include a Simple Network Paging Protocol (SNPP), a Telelocator Alphanumeric Protocol (TAP), FLEX, ReFLEX, Post Office Code Standardisation Advisory Group (POCSAG), GOLAY, Enhanced Radio Messaging System (ERMS), and NTT. For example, the communication module 202 may transmit the one or more encryption keys to the auxiliary device via a VHF or UHF signal, and wherein the auxiliary device contains one or more antenna(s) 406 configured to receive and recognize signals in the VHF and UHF frequency range, as depicted in FIG. 4.

At operation 310, the encryption module 204 encrypts the data object based on at least one encryption key form among the one or more encryption keys generated in response to the message to access the data object. For example, a first encryption key from among the one or more encryption keys may be selected based on a sequence of the one or more encryption keys. In some embodiments, responsive to encrypting the data object based on the encryption key, the encryption module 204 stores a copy of the encrypted data object with the request instance associated with the request from the client device 110 at the databases 126.

At operation 312, the presentation module 206 communicates a presentation of the encrypted data object to the client device 110. The client device 110 may then retrieve the corresponding encryption key associated with the encrypted data object from the auxiliary device to decrypt the data object and display the presentation of the data object.

Figure 4:
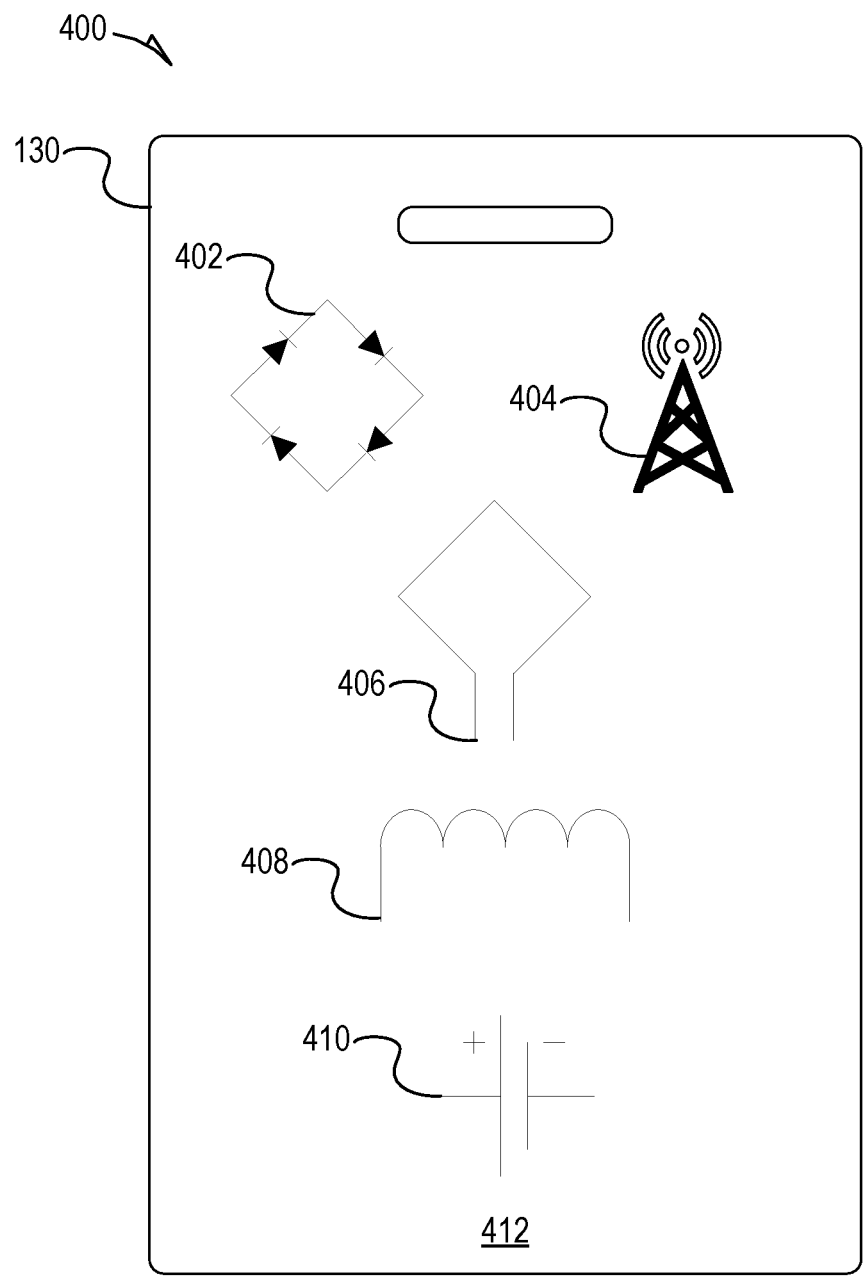
FIG. 4 is a diagram illustrating various functional components of a pager module, according to some example embodiments.

FIG. 4 is a diagram 400 illustrating various functional components of a pager module 130. As seen in the diagram 400, the pager module 130 may comprise a demodulator 402, a transmitter 404, antenna(s) 406, an inductive charging coil 408, and a battery 410, all enclosed within an enclosure 412.

In some example embodiments, the demodulator 402 includes a Frequency Shift Keying (FSK) Demodulator, configured to transmit digital information (e.g., message data) through discrete frequency changes of a carrier signal.

In some example embodiments, the transmitter 404 includes a short wave radio frequency transmitter (e.g., Bluetooth), configured to forward message data between the pager module 130 and a paired client device 110.

In some example embodiments the antenna(s) 406 include any one or a combination of a loop antenna consisting of a loop of wire, and fully enclosed by the enclosure 412. In some example embodiments, the antenna(s) 406 are integrated into a portion of the enclosure 412. For example, the enclosure 412 may comprise multiple components that come together to form the enclosure 412. In some embodiments, the antenna(s) 406 may be molded or formed into one or more of the components of the enclosure 412.

In some example embodiments, the antenna(s) 406 may be formed into a frame that encompasses a perimeter of a surface of the enclosure 412.

In some example embodiments, the charging coil 408 includes one or more exposed charging leads to enable a use to plug the pager module 130 into an outlet (e.g., USB).

In some example embodiments, the enclosure 412 is the form of a proximity card, such as a contactless smart card.

Figure 5:
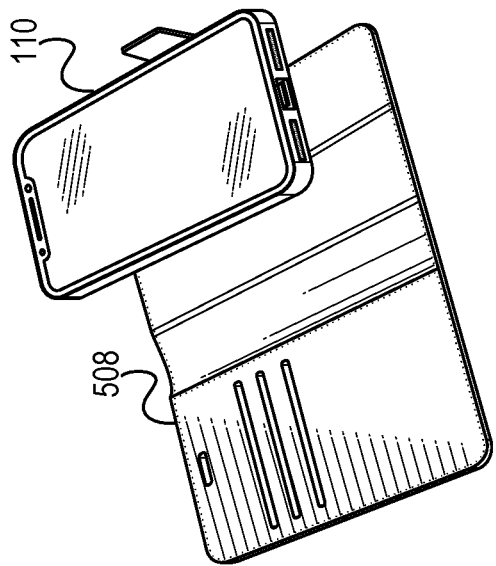
FIG. 5 is a diagram illustrating various embodiments of a pager module, according to some example embodiments.
Figure 5:
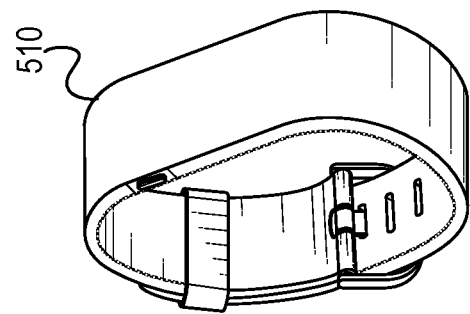
Figure 5:
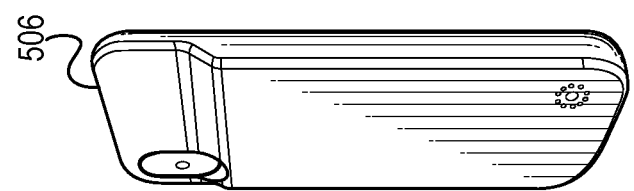
Figure 5:
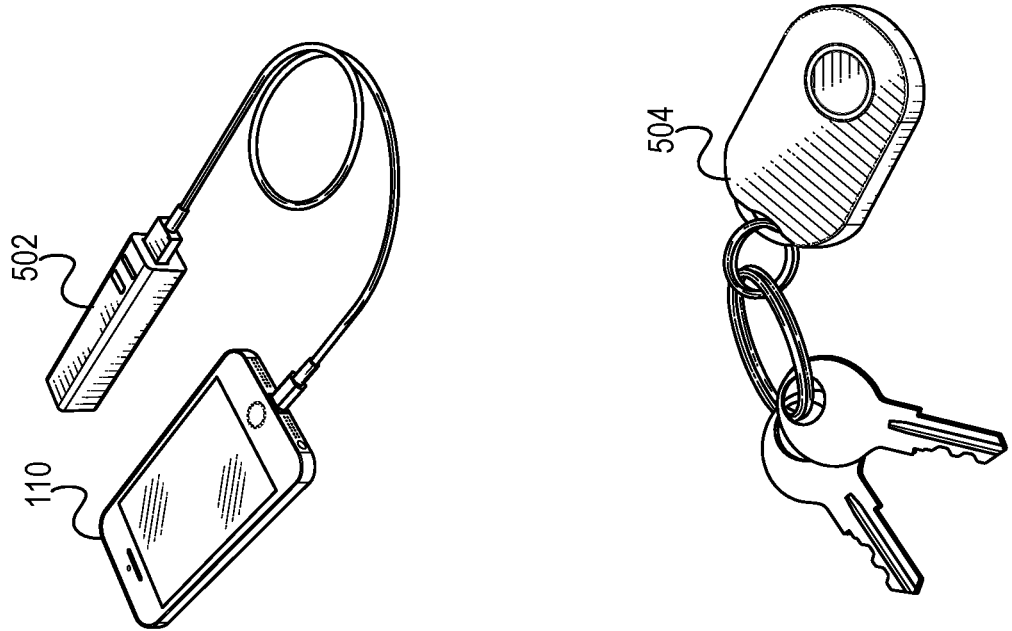

FIG. 5 is a diagram illustrating various embodiments of a pager module 130. As seen in FIG. 5, the enclosure 412 of the pager module 130 may include a number of different forms. In some example embodiments, the pager module 130 itself may comprise a modular unit which may be inserted within a number of distinct enclosures (e.g., the enclosure 412 of FIG. 4).

In some example embodiments, the enclosure 412 that houses the pager module 130 (as seen in FIG. 4) may include the tethered enclosure 502, wherein the tethered enclosure 502 may be communicatively coupled to the client device 110 via a cable. In some embodiments, the tethered enclosure 502 may include an extended battery unit to provide power to both the client device 110, as well as the pager module 130.

For example, the tethered enclosure 502 may comprise a metallic, or non-metallic housing that includes a connection port to receive a cable, such as a Universal Serial Bus Type-A (USB A) cable, USB Type-B, Mini-USB, Micro-USB, and USB Type-C. A user 106 of a client device 110 may connect the pager module 130 to the client device 110 via the tethered enclosure 502, through the integrated connection port.

Figure 6:
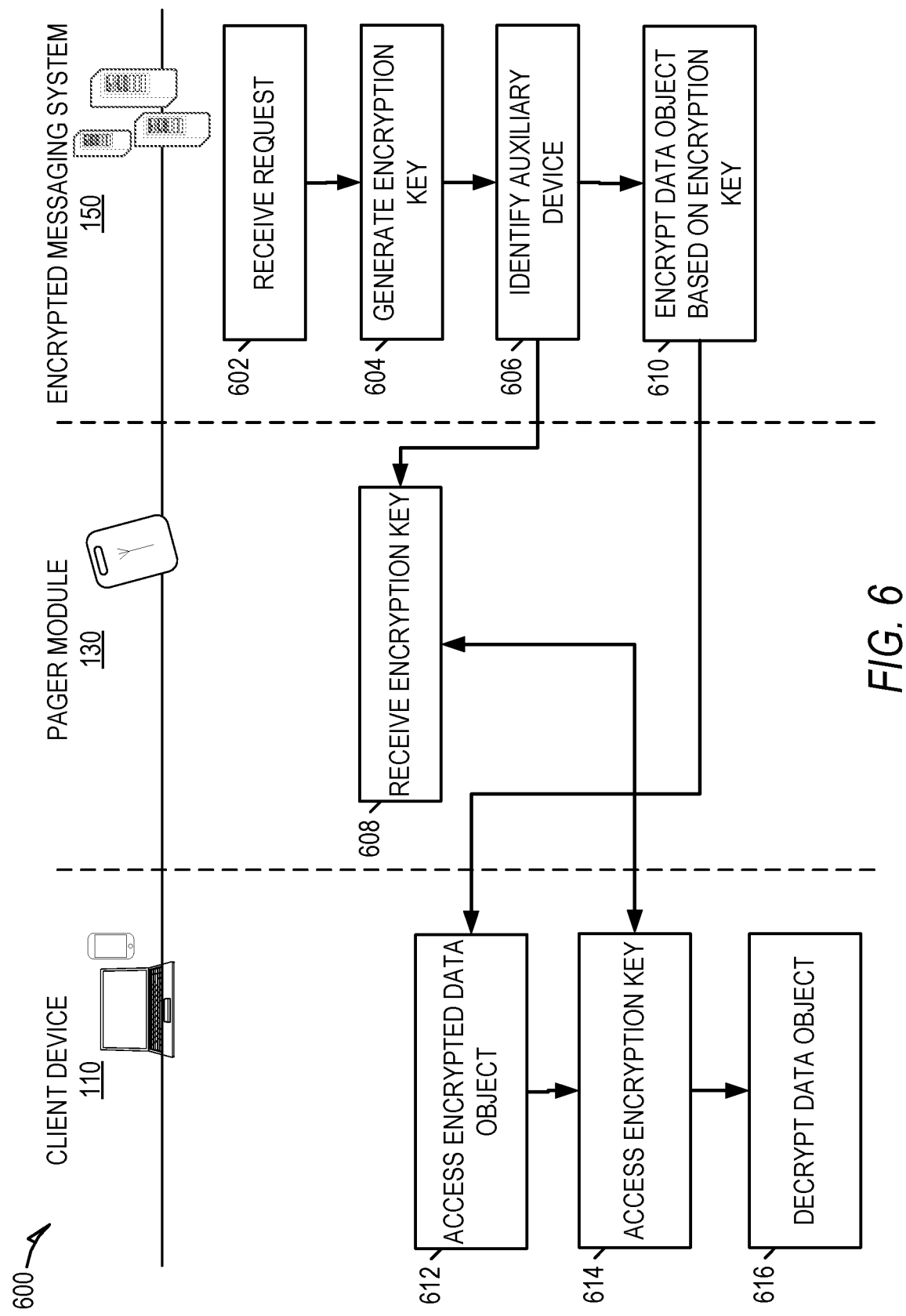
FIG. 6 is an interaction diagram illustrating a flow of data between an encrypted messaging system, a pager module, and a client device, according to some example embodiments.

In some example embodiments, the enclosure 412 that houses the pager module 130 (as seen in FIG. 6) may include a key-fob 504. The key-fob 504 may comprise a hook or loop to detachably receive a key-ring.

In some example embodiments, the enclosure 412 that houses the pager module 130 (as seen in FIG. 4) may include a cell-phone case 506, wherein the client device 110 may be inserted into the cell-phone case 506. In further embodiments, the cell-phone case 506 may include an integrated extended battery that supplies battery power to both the pager module 130 as well as the client device 110.

The cell-phone case 506 may comprise a semi-flexible housing to enclose a device, such as the client device 110, wherein the semi-flexible housing encases the client device 110, while exposing a screen of the client device 110.

In some example embodiments, the enclosure 412 that houses the pager module 130 (as seen in FIG. 6) may include a bi-fold case 508, wherein the client device 110 may be inserted into the bi-fold case 508. The bi-fold case 508 may comprise a housing to encase the client device 110, as well as a flap to cover a screen of the client device 110.

In some example embodiments, the enclosure 412 that houses the pager module 130 (as seen in FIG. 4) may include a band 510 (e.g., a wrist-band, an arm-band), wherein the band 510 may be worn by a user 106. The band 510 may comprise a fastener, such as a Velcro strap, an elastic band, buckle, tang buckle, deployment clasp, or pushbutton deployment clasp.

FIG. 6 is an interaction diagram 600 illustrating a flow of data, and various interactions between the encrypted messaging system 150, the pager module 130, and a client device 110, according to some example embodiments.

At operation 602, the encrypted messaging system 150 receives a request. For example, the request may include a message from a third-party, and may include message content, media content, and an identification of the client device 110. In further embodiments, the request may be from the client device 110 to access a data object hosted at a third party media repository, and may include an identification of the third party media repository and an identification of the data object.

At operation 604, responsive to receiving the request, the encrypted messaging system generates an encryption key. The encryption key may be generated based on one or more attributes of the client device 110, or based on one or more attributes of the pager module 130. For example, the user 106 may provide an input that defines public variables to be used by the encrypted messaging system 150 to generate an encryption key, and store the public variables at the pager module 130.

At operation 606, responsive to generating the encryption key, the encrypted messaging system 150 identifies an auxiliary device coupled with the client device 110, based on the request including the identification of the client device 110. In some embodiments, the database 126 may include a reference table that comprises associations between auxiliary devices and client device. The encrypted messaging system 150 may reference the table and identify an auxiliary device (e.g., the pager module 130) associated with the identifier of the client device 110.

At operation 608, the encrypted messaging system 150 transmits the encryption key to the pager module 130 (i.e., the auxiliary device). In certain embodiments, the encrypted messaging system 150 may transmit the encryption key to the pager module 130 via a predefined frequency associated with the pager module 130. For example, the reference table referenced by the encrypted messaging system 150 may include an identification of one or more transmission frequencies associated with the pager module 130, which may include frequencies in the VHF and UHF bands.

At operation 610, the encrypted messaging system 150 encrypts a data object based on the encryption key. In some embodiments, the encrypted messaging system 150 may access a third party repository to retrieve the data object, and store an encrypted copy of the data object locally. In further embodiments, the encrypted messaging system 150 may simply receive the data object (such as a message) and encrypt and store the data object with the databases 126.

At operation 612, the client device 110 receives a notification that comprises an identification of the data object. For example, the identification may include a reference to a location of the data object (or copy of the data object) at the encrypted messaging system 150.

At operation 614, the client device 110 accesses the pager module 130 coupled to the client device 110 to retrieve the encryption key that corresponds with the encrypted data object. For example, in certain embodiments, the pager module 130 may store a plurality of encryption keys, where each encryption key is associated with a particular request instance, such that the client device 110 may identify a particular encryption key for a data object based on an identifier of the request instance.

At operation 616, the client device 110 decrypts the data object based on the encryption key and displays a presentation of the decrypted data object. In some embodiments, functionality to decrypt the data object may also reside within the pager module 130, such that the pager module 130 acts as a "decryption tunnel," to provide encrypted communications between the client device 110 and the encrypted messaging system 150.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA)

or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Electronic Apparatus and System

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 7:
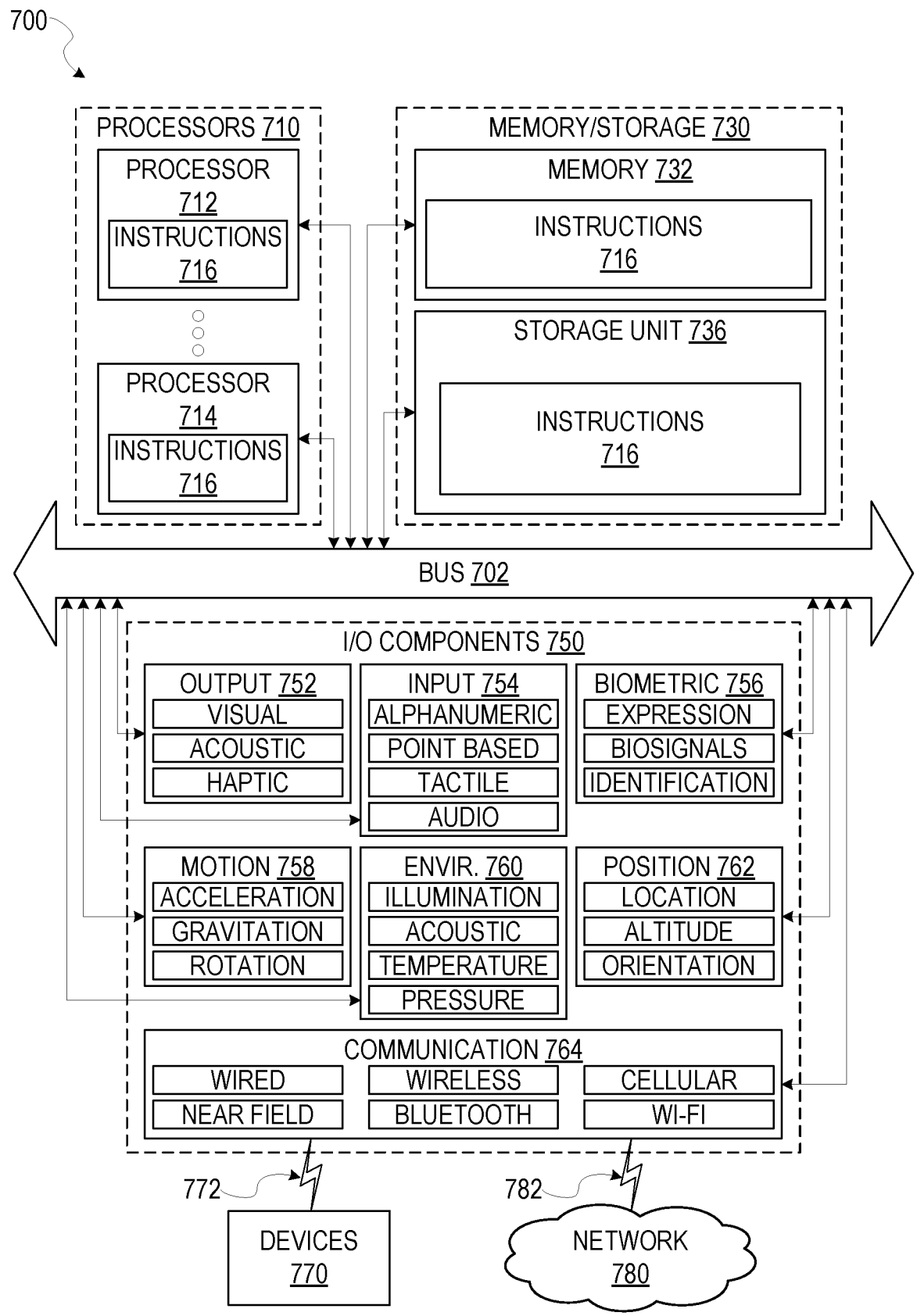
FIG. 7 is a diagrammatic representation of a machine in the example form of a computer system within which a set of instructions may be executed for causing the machine to perform any one or more of the methodologies discussed herein.

FIG. 7 is a block diagram illustrating components of a machine 700, according to some example embodiments, able to read instructions from a machine-readable medium (e.g., a machine-readable storage medium) and perform any one or more of the methodologies discussed herein. Specifically, FIG. 7 shows a diagrammatic representation of the machine 700 in the example form of a computer system, within which instructions 716 (e.g., software, a program, an application, an applet, an app, or other executable code) for causing the machine 700 to perform any one or more of the methodologies discussed herein may be executed. Additionally, or alternatively, the instructions may implement the modules of FIG. 2. The instructions transform the general, non-programmed machine into a specially configured machine programmed to carry out the described and illustrated functions in the manner described. In alternative embodiments, the machine 700 operates as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment.

The machine 700 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 716, sequentially or otherwise, that specify actions to be taken by machine 700. Further, while only a single machine 700 is illustrated, the term "machine" shall also be taken to include a collection of machines 700 that individually or jointly execute the instructions 716 to perform any one or more of the methodologies discussed herein.

The machine 700 includes processors 710, memory 730, and I/O components 750, which may be configured to communicate with each other such as via a bus 702. In an example embodiment, the processors 710 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 712 and processor 714 that may execute instructions 716. The term "processor" is intended to include multi-core processor that may comprise two or more independent processors (sometimes referred to as "cores") that may execute instructions contemporaneously. Although FIG. 7 shows multiple processors, the machine 700 may include a single processor with a single core, a single processor with multiple cores (e.g., a multi-core process), multiple processors with a single core, multiple processors with multiples cores, or any combination thereof.

The memory/storage 730 may include a memory 732, such as a main memory, or other memory storage, and a storage unit 736, both accessible to the processors 710 such as via the bus 702. The storage unit 736 and memory 732 store the instructions 716 embodying any one or more of the methodologies or functions described herein. The instructions 716 may also reside, completely or partially, within the memory 732, within the storage unit 736, within at least one of the processors 710 (e.g., within the processor's cache memory), or any suitable combination thereof, during execution thereof by the machine 700. Accordingly, the memory 732, the storage unit 736, and the memory of processors 710 are examples of machine-readable media.

As used herein, "machine-readable medium" means a device able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 716. The term "machine-readable medium" shall also be taken to include any medium, or combination of multiple media, that is capable of storing instructions (e.g., instructions 716) for execution by a machine (e.g., machine 700), such that the instructions, when executed by one or more processors of the machine 700 (e.g., processors 710), cause the machine 700 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes transitory signals per se.

The I/O components 750 may include a wide variety of components to receive input, provide output, produce output, transmit information, exchange information, capture measurements, and so on. The specific I/O components 750 that are included in a particular machine will depend on the type of machine. For example, portable machines such as mobile phones will likely include a touch input device or other such input mechanisms, while a headless server machine will likely not include such a touch input device. It will be appreciated that the I/O components 750 may include many other components that are not shown in FIG. 7. The I/O components 750 are grouped according to functionality merely for simplifying the following discussion and the grouping is in no way limiting. In various example embodiments, the I/O components 750 may include output components 752 and input components 754. The output components 752 may include visual components (e.g., a display such as a plasma display panel (PDP), a light emitting diode (LED) display, organic light-emitting diode (OLED), a liquid crystal display (LCD), a projector, or a cathode ray tube (CRT)), electronic paper (e-paper), acoustic components (e.g., speakers), haptic components (e.g., a vibratory motor, resistance mechanisms), other signal generators, and so forth. The input components 754 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 750 may include biometric components 756, motion components 758, environmental components 760, or position components 762 among a wide array of other components. For example, the biometric components 756 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 758 may include acceleration sensor components (e.g., accelerometer), gravitation sensor components, rotation sensor components (e.g., gyroscope), and so forth. The environmental components 760 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 762 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 750 may include communication components 764 operable to couple the machine 700 to a network 780 or devices 770 via coupling 782 and coupling 772 respectively. For example, the communication components 764 may include a network interface component or other suitable device to interface with the network 780. In further examples, communication components 764 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 770 may be another machine or any of a wide variety of peripheral devices (e.g., a peripheral device coupled via a Universal Serial Bus (USB)).

Moreover, the communication components 764 may detect identifiers or include components operable to detect identifiers. For example, the communication components 764 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 764, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 780 may be an ad hoc network, an intranet, an extranet, a pager network, a Simple Network Paging Protocol (SNPP), a Telelocator Alphanumeric Protocol (TAP), FLEX, ReFLEX, Post Office Code Standardisation Advisory Group (POCSAG), GOLAY, Enhanced Radio Messaging System (ERMS), and NTT, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 780 or a portion of the network 780 may include a wireless or cellular network and the coupling 782 may be a Code Division Multiple Access (CDMA) connection, a Global System for Mobile communications (GSM) connection, or other type of cellular or wireless coupling. In this example, the coupling 782 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 716 may be transmitted or received over the network 780 using a transmission medium via a network interface device (e.g., a network interface component included in the communication components 764) and utilizing any one of a number of well-known transfer protocols (e.g., hypertext transfer protocol (HTTP)). Similarly, the instructions 716 may be transmitted or received using a transmission medium via the coupling 772 (e.g., a peer-to-peer coupling) to devices 770. The term "transmission medium" shall be taken to include any intangible medium that is capable of storing, encoding, or carrying instructions 716 for execution by the machine 700, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A method comprising:
   receiving a request to access a data record stored within a database, the request including a user identifier;
   generating an encryption key in response to the receiving the request to access the data record;
   assigning the encryption key to a request instance associated with the request to access the data record at a user account identified by the user identifier;
   identifying an access restriction associated with the data record, the access restriction including a condition;
   applying the condition of the access restriction to the encryption key at the request instance associated with the request to access the data record;
   encrypting the data record using the encryption key assigned to the request instance within the user account identified by the user identifier responsive to the request to access the data record that includes the user identifier;
   communicating a presentation of the encrypted data record to a client device associated with the user account;
   detecting the condition of the access restriction; and
   denying the request to access the data record.

2. The method of claim 1, wherein the condition includes a temporal constraint that comprises a period of time, and the detecting the condition includes:
   detecting an expiration of the period of time.

3. The method of claim 1, wherein the denying the request to access the data record includes:
   deleting the encryption key from the request instance within the user account identified by the user identifier in response to the detecting the condition.

4. The method of claim 1, wherein the request is a first request, the user identifier is a first user identifier, the user account is a first user account, the request instance is a first request instance, the encryption key is a first encryption key, the client device is a first client device, and the method further comprises:
   receiving a second request to access the data record, the second request including a second user identifier;
   generating a second encryption key in response to the receiving the second request to access the data record;
   assigning the second encryption key to a second request instance associated with the second request to access the data record at a second user account identified by the second user identifier;
   encrypting the data record using the second encryption key assigned to the second request instance within the second user account identified by the second user identifier responsive to the second request to access the data record that includes the second user identifier; and
   communicating the presentation of the encrypted data record to a second client device associated with the second user account.

5. The method of claim 1, wherein the method further comprises:
   maintaining a record of the request to access the data record responsive to receiving the request to access the data record, the record including at least an identification of the user identifier and a timestamp.

6. The method of claim 1, wherein the request to access the data record is a first request, the data record includes a reference identifier, and the method further comprises:
   encrypting the reference identifier of the data record based on the encryption key assigned to the request instance within the user account identified by the user identifier, responsive to the request to access the data record that includes the user identifier;
   communicating the encrypted reference identifier to the client device associated with the user account via a first communication protocol;
   receiving a second request to access the data record from the client device via a second communication protocol, the second request including the encrypted reference identifier; and
   communication the presentation of the encrypted data record to the client device associated with the user account via the second communication protocol.

7. A system comprising:
   one or more processors;
   an auxiliary device coupled with a client device; and
   a memory storing instructions that, when executed by at least one processor among the one or more processors, cause the system to perform operations comprising:
   receiving, from the client device, a request to access a data record stored within a database, the request including a user identifier;
   generating an encryption key in response to the receiving the request to access the data record;
   assigning the encryption key to a request instance associated with the request to access the data record at a user account identified by the user identifier;
   identifying an access restriction associated with the data record, the access restriction including a condition;
   applying the condition of the access restriction to the encryption key at the request instance associated with the request to access the data record;
   encrypting the data record using the encryption key assigned to the request instance within the user account identified by the user identifier responsive to the request to access the data record that includes the user identifier;
   communicating a presentation of the encrypted data record to a client device associated with the user account;
   detecting the condition of the access restriction; and
   denying the request to access the data record.

8. The system of claim 7, wherein the condition includes a temporal constraint that comprises a period of time, and the detecting the condition includes:
  detecting an expiration of the period of time.

9. The system of claim 7, wherein the denying the request to access the data record includes:
  deleting the encryption key from the request instance within the user account identified by the user identifier in response to the detecting the condition.

10. The system of claim 7, wherein the request is a first request, the user identifier is a first user identifier, the user account is a first user account, the request instance is a first request instance, the encryption key is a first encryption key, the client device is a first client device, and the operations further comprise:
  receiving a second request to access the data record, the second request including a second user identifier;
  generating a second encryption key in response to the receiving the second request to access the data record;
  assigning the second encryption key to a second request instance associated with the second request to access the data record at a second user account identified by the second user identifier;
  encrypting the data record using the second encryption key assigned to the second request instance within the second user account identified by the second user identifier responsive to the second request to access the data record that includes the second user identifier; and
  communicating the presentation of the encrypted data record to a second client device associated with the second user account.

11. The system of claim 9, wherein the operations further comprise:
  maintaining a record of the request to access the data record responsive to receiving the request to access the data record, the record including at least an identification of the user identifier and a timestamp.

12. The system of claim 7, wherein the request to access the data record is a first request, the data record includes a reference identifier, and the operations further comprise:
  encrypting the reference identifier of the data record based on the encryption key assigned to the request instance within the user account identified by the user identifier, responsive to the request to access the data record that includes the user identifier;
  communicating the encrypted reference identifier to the client device associated with the user account via a first communication protocol;
  receiving a second request to access the data record from the client device via a second communication protocol, the second request including the encrypted reference identifier; and
  communication the presentation of the encrypted data record to the client device associated with the user account via the second communication protocol.

13. A non-transitory machine-readable storage device storing instructions that, when executed by one or more processors, cause the one or more processors to perform operations comprising:
  receiving a request to access a data record stored within a database, the request including a user identifier;
  generating an encryption key in response to the receiving the request to access the data record;
  assigning the encryption key to a request instance associated with the request to access the data record at a user account identified by the user identifier;
  identifying an access restriction associated with the data record, the access restriction including a condition;
  applying the condition of the access restriction to the encryption key at the request instance associated with the request to access the data record;
  encrypting the data record using the encryption key assigned to the request instance within the user account identified by the user identifier responsive to the request to access the data record that includes the user identifier;
  communicating a presentation of the encrypted data record to a client device associated with the user account;
  detecting the condition of the access restriction; and
  denying the request to access the data record.

14. The non-transitory machine-readable storage device of claim 13, wherein the condition includes a temporal constraint that comprises a period of time, and the detecting the condition includes:
  detecting an expiration of the period of time.

15. The non-transitory machine-readable storage device of claim 13, wherein the denying the request to access the data record includes:
  deleting the encryption key from the request instance within the user account identified by the user identifier in response to the detecting the condition.

16. The non-transitory machine-readable storage device of claim 13, wherein the request is a first request, the user identifier is a first user identifier, the user account is a first user account, the request instance is a first request instance, the encryption key is a first encryption key, the client device is a first client device, and the operations further comprise:
  receiving a second request to access the data record, the second request including a second user identifier;
  generating a second encryption key in response to the receiving the second request to access the data record;
  assigning the second encryption key to a second request instance associated with the second request to access the data record at a second user account identified by the second user identifier;
  encrypting the data record using the second encryption key assigned to the second request instance within the second user account identified by the second user identifier responsive to the second request to access the data record that includes the second user identifier; and
  communicating the presentation of the encrypted data record to a second client device associated with the second user account.

17. The non-transitory machine-readable storage device of claim 13, wherein the operations further comprise:
  maintaining a record of the request to access the data record responsive to receiving the request to access the data record, the record including at least an identification of the user identifier and a timestamp.

* * * * *

UNITED STATES PATENT AND TRADEMARK OFFICE
CERTIFICATE OF CORRECTION

PATENT NO. : 11,074,997 B2  
APPLICATION NO. : 16/377564  
DATED : July 27, 2021  
INVENTOR(S) : Okajima et al.

Page 1 of 1

It is certified that error appears in the above-identified patent and that said Letters Patent is hereby corrected as shown below:

In the Claims

In Column 19, Line 32, in Claim 11, delete "claim 9," and insert --claim 7,-- therefor Signed and Sealed this  
Second Day of November, 2021

Drew Hirshfeld  
*Performing the Functions and Duties of the*  
*Under Secretary of Commerce for Intellectual Property and*  
*Director of the United States Patent and Trademark Office*